(12) United States Patent
Manetakis et al.

(10) Patent No.: US 6,840,945 B2
(45) Date of Patent: Jan. 11, 2005

(54) MEDICAL CLIP APPLIER SAFETY ARRANGEMENT

(75) Inventors: Emmanuel Manetakis, Burlington, MA (US); Henri de Guillebon, Manchester, MA (US)

(73) Assignee: Microline, Inc., Beverly, MA (US)

(*) Notice: Subject to any disclaimer, the term of this patent is extended or adjusted under 35 U.S.C. 154(b) by 283 days.

(21) Appl. No.: 10/085,737

(22) Filed: Feb. 28, 2002

(65) Prior Publication Data
US 2002/0128668 A1 Sep. 12, 2002

Related U.S. Application Data

(63) Continuation-in-part of application No. 09/934,378, filed on Aug. 21, 2001, now Pat. No. 6,569,171, and a continuation-in-part of application No. 09/795,808, filed on Feb. 28, 2001, now Pat. No. 6,620,184.

(51) Int. Cl.[7] .............................................. A61B 17/10
(52) U.S. Cl. ........................ 606/142; 606/139; 606/143
(58) Field of Search .................................. 606/139, 142, 606/143, 219, 221; 227/175.1

(56) References Cited

U.S. PATENT DOCUMENTS 6,599,298 B1 * 7/2003 Forster et al. .............. 606/139

* cited by examiner

*Primary Examiner*—Julian W. Woo
(74) *Attorney, Agent, or Firm*—Don Halgren

(57) ABSTRACT

A medical clip dispenser apparatus for the pinching of a medical clip or staple about a portion of a mammalian body tissue. The apparatus comprises an elongated support beam having a distal end with a stationary lower housing thereon, and a distally movable hollow cinch slidably disposed on the lower housing. The cinch has a portion of a pair of closable jaws squeezably arranged therewithin. An elongated pusher has a generally cross-shaped pusher member on a distal end thereof in slidable engagement with the jaws, to keep the jaws apart from one another after a new clip has been pushed into position between the jaws.

11 Claims, 11 Drawing Sheets

MEDICAL CLIP APPLIER SAFETY ARRANGEMENT

This application is a continuation-in-part of Ser. No. 09/934,378 filed Aug. 21, 2001, now U.S. Pat. No. 6,569,171 and is a continuation-in-part of Ser. No. 09/795,808 filed Feb. 28, 2001 now U.S. Pat. No. 6,620,184.

BACKGROUND OF THE INVENTION

1. Field of the Invention

This invention relates to medical clip devices and more particularly to guidance and alignment arrangements on the tip of those medical clip devices, and is co-pending with and a continuation in part of commonly assigned U.S. patent applications Ser. Nos. 09/795,808, entitled "Release Mechanism for a Grasping Device" filed Feb. 28, 2001 and Serial No. 09/934,378, entitled "Safety Locking Mechanism for a Medical Clip Device" and filed Aug. 21, 2001, as all of which are incorporated herein by reference in their entirety.

2. Prior Art

Medical clip devices are utilized to pinch and shut off a body tissue. The clip device usually comprises an elongated support arm having a distal end comprising a pair of squeezable jaws. Medical clip devices are shown in U.S. Pat. Nos. 6,277,131 to Kalikow, and Ser. No. 6,306,141 to Meade, each of which are also incorporated herein by reference. Typically a staple or squeezable wire is pushed tightly between those jaws once the jaws and "still open" staple has surrounded a body tissue to be pinched/shut off. A problem arises occasionally wherein the staple or clip may slip from those jaws as those jaws are unintentionally manipulated and the staple gets lost at the body treatment site.

It is an object of the present invention to provide improvement over prior art medical clip applying devices.

It is a further object of the present invention to provide a medical clip device which minimizes any problems associated with clip misalignment with respect to the jaws or with a possible loss of a clip by a mis-firing occurring within that clip device.

BRIEF SUMMARY OF THE INVENTION

The present invention relates to an improvement of the jaw mechanism of a medical clip-applying device. Such a medical clip applying device comprises an elongated beam having a proximal end and a distal end. A pistol-like handle is arranged at the proximal end, with a trigger mechanism arranged with an elongated coupling connected to the jaws so as to permit the jaws to be squeezed together as the attending physician pulls on the trigger. The jaws are biased into the spread-apart or open position and have to be squeezed together for them to pinch a clip or staple, as will be described hereinbelow.

A pusher mechanism is arranged with the handle, the pusher having a distalmost end, which sequentially pushes clips into a position between the jaws before the jaws are squeezed together at the distalmost end of the medical clip device. The distalmost end of the pusher in this invention has a generally cross-shaped member, having a pair of wings thereon. The elongated cross-shaped portion has a pair of opposed upstanding rails on the distalmost end of the crossed-shaped member.

The upstanding rails each have a proximal sloping edge which permits the cross-shaped member to be cammed downwardly and out of the way of the clip supply when the cross-shaped member is retracted proximally as it moves, in order to engage a successive medical clip or staple to be squeezed between the jaws. The upstanding members each have a distalmost edge which engages the proximal end or bridging portion of the U-shaped clip or staple as it is pushed into the receiving tracks of the opposed jaws on the distal end of the medical clip device.

The jaws are movably supported between an upper housing half, called a "cinch", and a stationary lower housing half called a "brace. The jaws each have an upstanding "limiting" pin on each leg thereof. Each pin is arranged to slide within a respective track disposed on an inner surface wall of the cinch, and each pin may be lodged into a pocket at the distal end of each track to limit or prevent inadvertent closure of the jaws at that point. The jaw pins, when slid into the pockets in the cinch thus prevent the jaws from accidentally closing or pinching a clip or staple between those jaws and force the jaws open before the clip goes between the jaws. The wings on the elongated cross-shaped push member fit into the same track in the jaws as do the generally U-shaped clips do as they are being pushed distally or forwardly and prevent the jaws from partially closing to otherwise partially squeeze a staple or clip and thus have the clip fall accidently into a patient. The outer edges of the wings slide between the jaws as they biasedly spread apart or open so as to enable it to receive the fully spread open generally U-shaped clip as it is being pushed therebetween. This opening of the jaws and distal motion by the outermost ends of the wings of the cross-shaped member occurs as the jaws are being permitted to reopen to accept a new, open U-shaped clip member, ready for a further clip actuation on body tissue. Those wings on the cross-shaped member and the pins on the jaws engaged in the pockets of the cinch work simultaneously to provide the locking open of the jaws for proper receipt of the U-shaped clip therebetween and for proper opposed alignment of the jaws.

The jaws are pushed to their squeezed-closed position by an arrangement of cam surfaces each rubbing against a surface of each leg of the jaws, the generally U-shaped (in cross section) cinch being pushed distally on the distal end of a "closing" pushrod. The pushrod is connected to the trigger mechanism in the proximal or handle end of the medical clip device.

The distalmost finger of the elongated spring is in rubbing, biased engagement with the underside of the generally cross-shaped pusher member. The biased spring thus also keeps the elongated cross-shaped pusher member in contact with the shoulders or ledges on the inner edges of each respective jaw and keeps the pusher member behind the clip during loading thereof so as to prevent slipping and misfiring of that clip. By maintaining a biased pressure against the jaws in that manner, the jaws are prevented from crossing or misaligning with one another when those jaws are being squeezed together and closing in on a U-shaped clip therebetween. The jaws are thus accurately "opposed" with respect to one another, because of their receipt of a biased pusher and alignment cross arranged therebetween.

The invention thus comprises a medical clip dispenser apparatus for the pinching of a medical clip or staple about a portion of a mammalian body tissue, the apparatus comprising an elongated support beam having a distal end with a stationary lower housing thereon; a distally movable hollow cinch slidably disposed on the lower housing, the cinch having a portion of a pair of closable jaws squeezably arranged therewithin; and an elongated push rod having a generally cross-shaped pusher member on a distal end thereof in slidable engagement with the jaws, to keep the jaws open and in alignment with one another and to concurrently push a new clip into position between the jaws.

Each of the jaws may have an inner edge with a shoulder extending therealong, for guided receipt of a clip and for stabilizing receipt of the cross-shaped pusher member. The cross-shaped member includes a pair of wing members extending therefrom, each of the wing members mating with the shoulder to keep the jaws spread apart after a clip has been fed therebetween. The cross-shaped member includes a pair of wings laterally disposed thereon, so as to slidably engage the shoulders in the jaws to keep the jaws open when the cross-shaped member is pushed distally, behind the clip when it is loaded, and to thus prevent the jaws from being inadvertently closed on a staple or clip therebetween.

Each of the wings may have an upstanding rail thereon, each of the rails having a distal edge arranged to push distally a new clip in a clip track during distal advancement of the cross-shaped member. Each of the rails may have a sloped proximal edge to permit the rails to be cammed downwardly and out of the way of the clip track during proximal movement of the cross-shaped member.

Each of the wings may have an outer edge thereon for respective engagement with each of the jaws during opening of the jaws during distal motion of the cross-shaped member with respect to the lower housing. Each of the jaws has an upstanding pin thereon for sliding engagement into a pocket in the cinch to prevent accidental closing of the jaws.

The lower housing or brace comprises the lower side of the stationary support. A spring, which is an elongated member having a distalmost end, is shaped upwardly and arranged to provide a biased finger on the lowermost side of the generally cross-shaped pusher member to keep it aligned and against the bridging portions of the staples or clips. The spring has a proximal end which is bifurcated into two parallel legs. The legs are formed into a generally U-shaped configuration in a longitudinal direction. The elongated arm of the clip pusher rod runs snugly between the bifurcated legs of the spring and is kept in longitudinal alignment thereby.

The medical clip dispenser may include the elongated biasing spring secured in the lower housing, the elongated biasing spring having a distal end which is in rubbing engagement with a lower side of the cross-shaped member so as to keep the cross-shaped member in a line behind the clip in the jaws. The elongated biasing spring may have a bifurcated proximal end, the bifurcated proximal end arranged to straddle the elongated pusher rod for alignment of the pusher rod and the cross-shaped member with respect to the spring.

The invention may also comprise a method for dispensing a medical clip onto a mammalian body tissue comprising: arranging a pair of closable jaws to be supported between a stationary lower housing and a movable upper housing of an elongated medical clip dispensing device; moving a pusher member between the jaws to slide between the jaws as they spread apart from one another and to concurrently push an open clip into position between the jaws in tracks or shoulders in the jaws; biasing the pusher member into said tracks in the jaws to keep the jaws in alignment by an elongated biasing spring on a lower side of the pusher member; and closing the jaws together by a distally advancing cinch to squeeze the jaws together and crimp the clip between the jaws onto a body tissue as the pusher member is withdrawn proximally from a position between said jaws. The cinch has a pair of cam track arrangements each of which includes the pocket for slidable capture and release of a pin therefrom to permit the jaws to be temporarily locked in the open position.

The method may include arranging an outer edge of each wing on the distal end of the pusher member into engagement with the jaws to facilitate the keeping open of the jaws after distal movement of the clip pusher member between the jaws, and after pushing a clip into position between the jaws by engagement of a pair of upstanding rails in the pusher member with a bridging portion of the clip.

The method may also include pushing a clip into position between the jaws by engagement of a pair of upstanding rails on the distal end of the pusher member against a bridging portion of the clip; arranging a pin on an intermediate portion of each of the jaws; arranging a pair of cam tracks in an inner surface of the cinch for slidable engagement with the pins on the jaws; biasedly locking open the jaws by cammed motion and receipt of the pins in a pocket arrangement in a distal end of the cam tracks in the inner surface of the cinch; arranging an elongated biasing spring in the brace of the lower housing, the biasing spring having a bifurcated proximal end and an upwardly directed distal end; and aligning the bifurcated end about the pusher member to maintain the pusher member in alignment with respect to the jaws; biasing the distal end of the biasing spring so as to keep the upstanding rails against the bridging portion of the clips during delivery thereof to the jaws; and engaging the pins in the cam track in the cinch to limit distal advance and proximal motion of the cinch with respect to the lower brace.

BRIEF DESCRIPTION OF THE DRAWINGS

The objects and advantages of the present invention will become more apparent when viewed in conjunction with the following drawings in which:

FIG. 3b is a side elevational view of the device shown in FIG. 3a;

FIG. 3c is a bottom view of the clip device shown in FIG. 3a;

FIG. 5b is a view taken along the lines 5b—5b of FIG. 5a;

FIG. 5c is a perspective view of the cinch shown in FIG. 5a;

DESCRIPTION OF THE PREFERRED EMBODIMENTS

Figure 1:
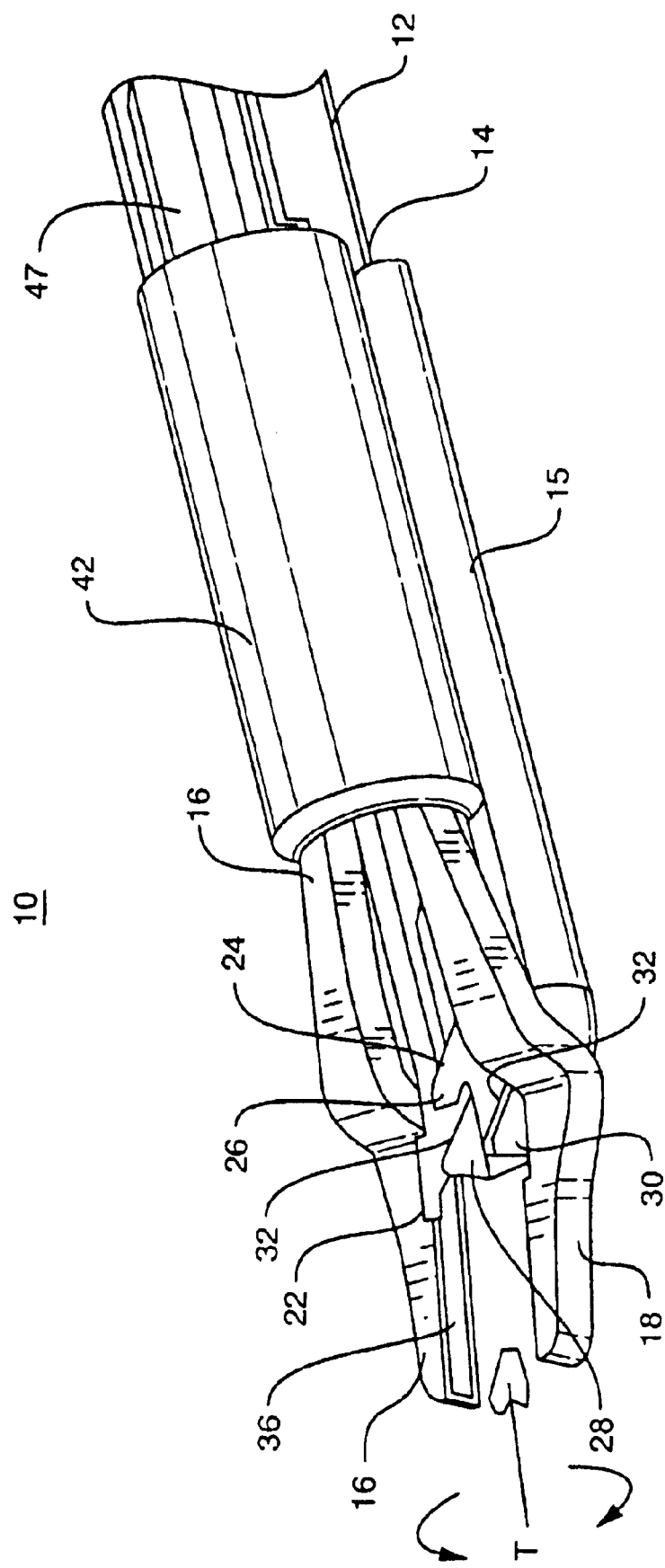
FIG. 1 is a perspective view of the distal end of the medical clip device of the present invention.

Referring now to the drawings and particularly to FIG. 1, there is shown the present invention which comprises a medical clip applying device 10 comprises an elongated beam 12 having a proximal end (not shown here for clarity) and a distal end 14 fixedly secured to a stationary lower housing or brace 15. A pistol-like handle (not shown) is arranged at the proximal end, with a trigger mechanism arranged with an elongated coupling connected to a pair of jaws 16 and 18 so as to permit the jaws 16 and 18 to be squeezed together as the attending physician pulls on the trigger.

A pusher mechanism is arranged with the handle (not shown for clarity), the pusher 20, as may be seen in FIGS. 2, 3b, 3c, 4 and 7, has a distalmost end, which sequentially pushes staples or clips 22, as shown in phantom in FIG. 1, into a position between the jaws 16 and 18 before the jaws 16 and 18 are squeezed together at the distalmost end of the medical clip device 10. The distalmost end of the pusher 20 in this invention has a generally cross-shaped member 24, having a pair of wings 26 thereon, as may be seen in FIGS. 1, 3a and 3c. The elongated cross-shaped member 24 has a pair of opposed upstanding rails 28 and 30, on the distalmost end of the crossed-shaped member 24, as may be seen in FIGS. 1, 2, 3a and 3c.

Figure 2:
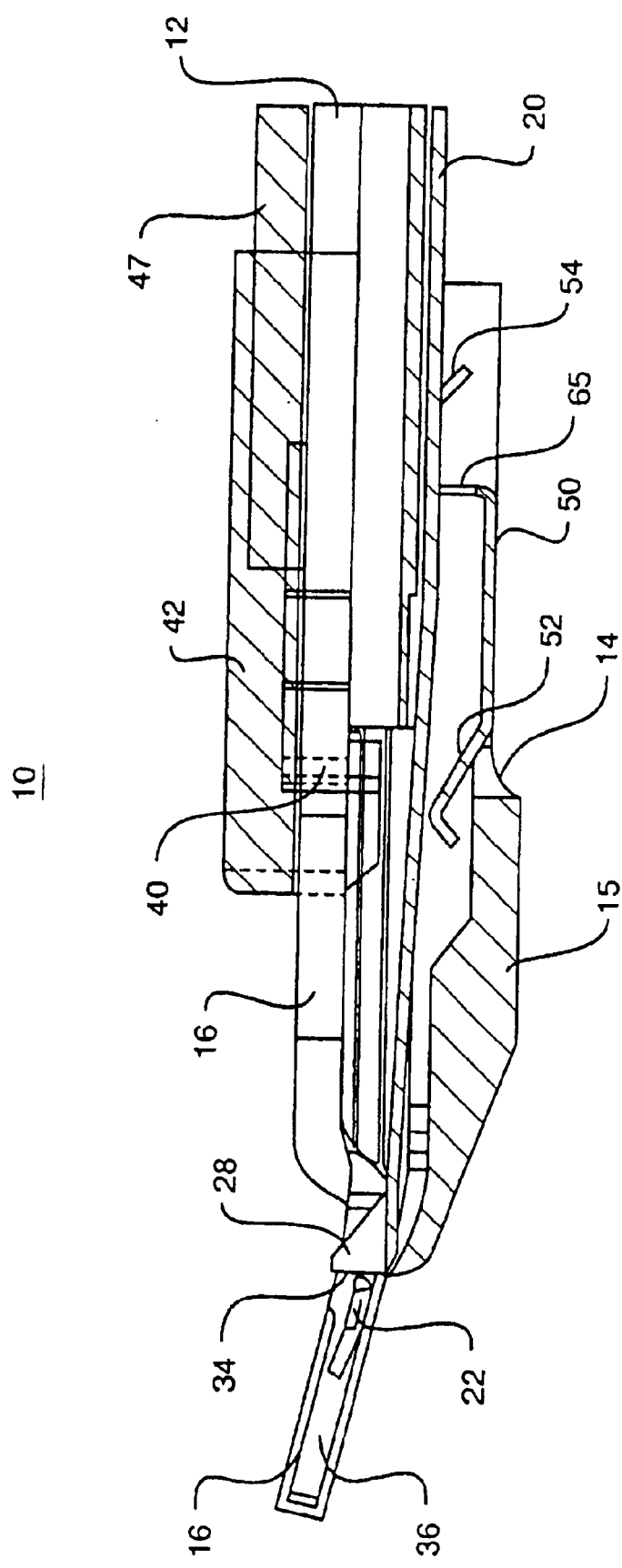
FIG. 2 is a side elevational view, in longitudinal central section of the clip device shown in FIG. 1.
Figure 3A:
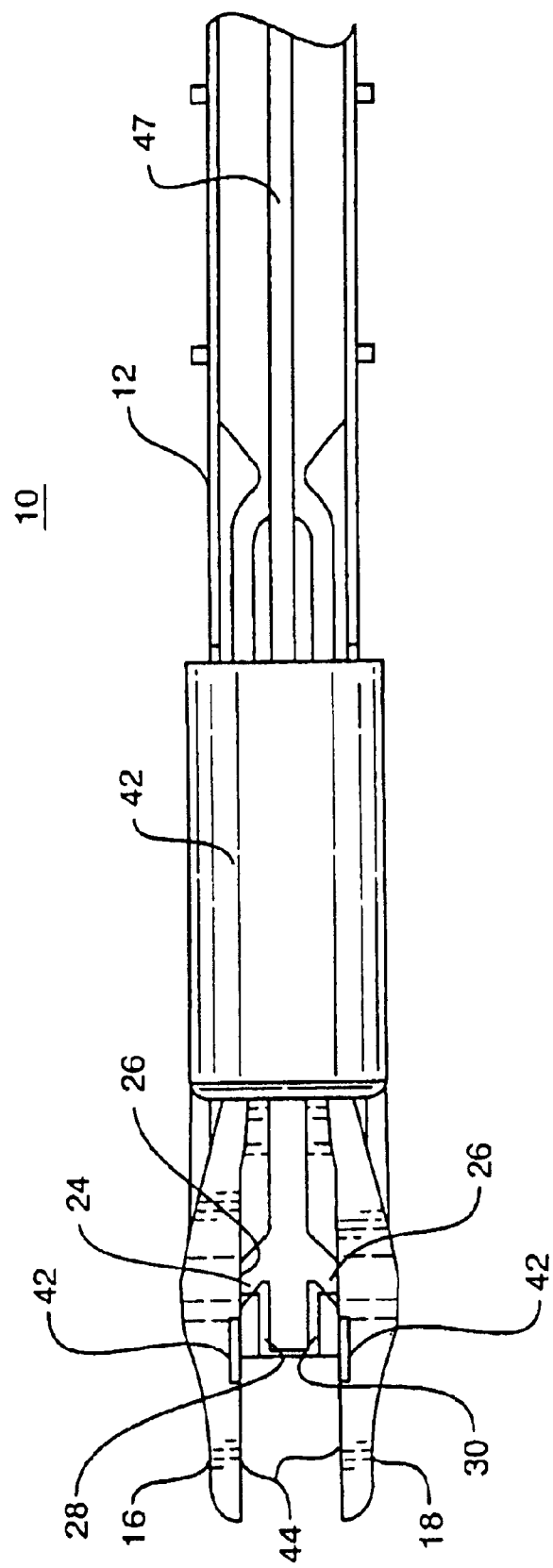
FIG. 3a is a plan view of the medical clip device shown in FIG. 1.
Figure 3B:
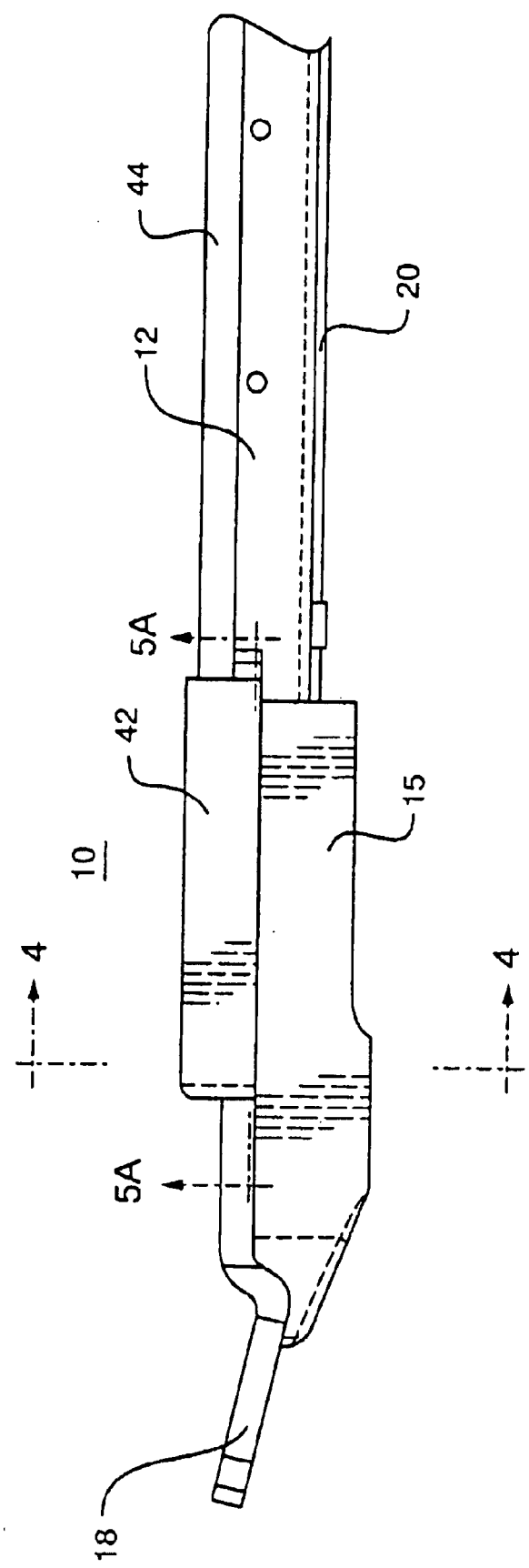
Figure 3C:
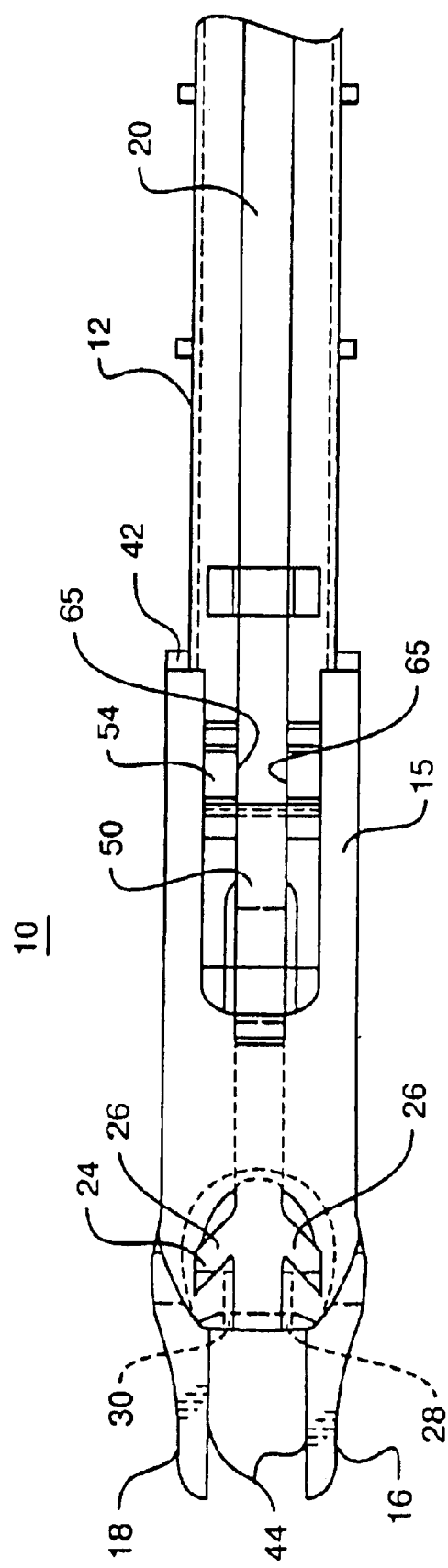

The upstanding rails 28 and 30 each have a proximal sloping edge 32 which permits the cross shaped member 24 to be cammed downwardly and out of the way of the clip supply when the cross-shaped member 24 is retracted proximally as it moves, in order to engage a successive medical clip or staple 22 to be sequentially squeezed between the jaws 16 and 18. The upstanding rails 28 and 30 each have a distalmost edge 34, as best shown in FIG. 2, which edge 34 engages the proximal or "bridging" end of the U-shaped clip or staple 22 as it is pushed into an arrangement of receiving tracks 36 of the opposed jaws 16 and 18 on the distal end of the medical clip device 10.

Figure 4:
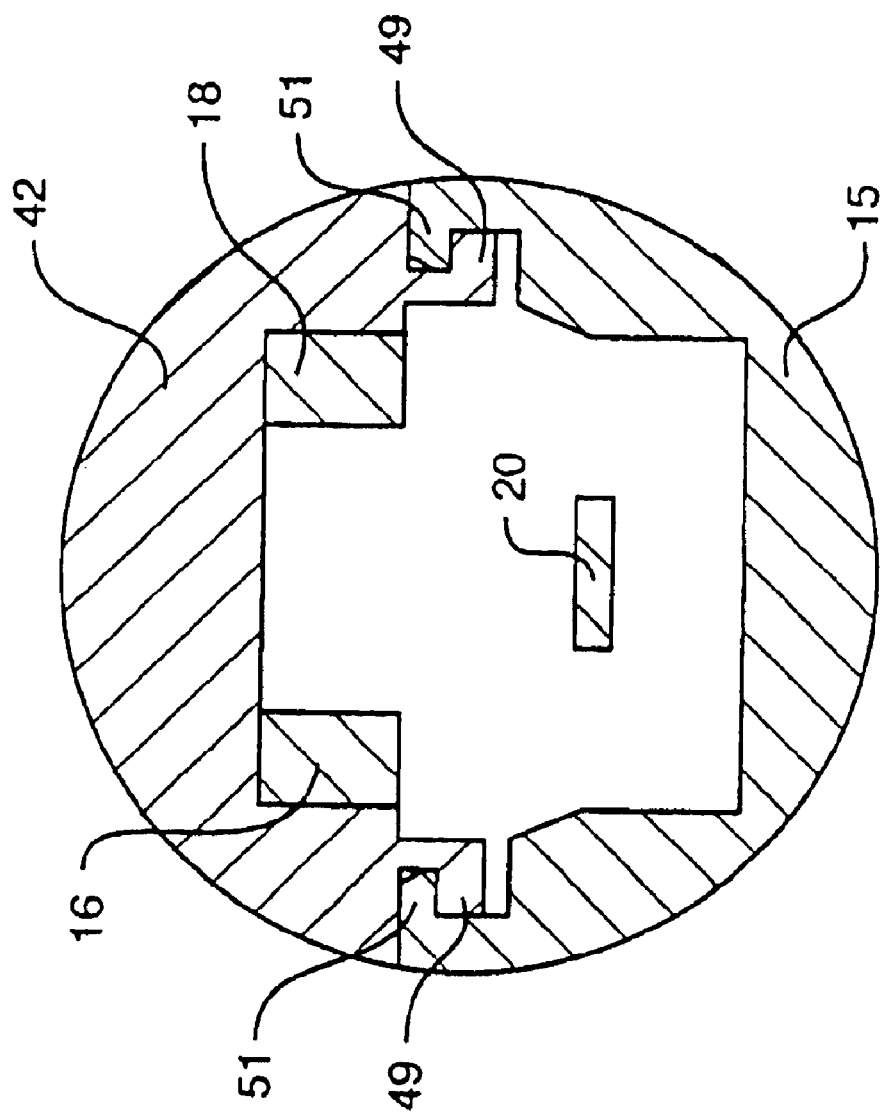
FIG. 4 is a view taken along the lines 4—4 of FIG. 3b.
Figure 5A:
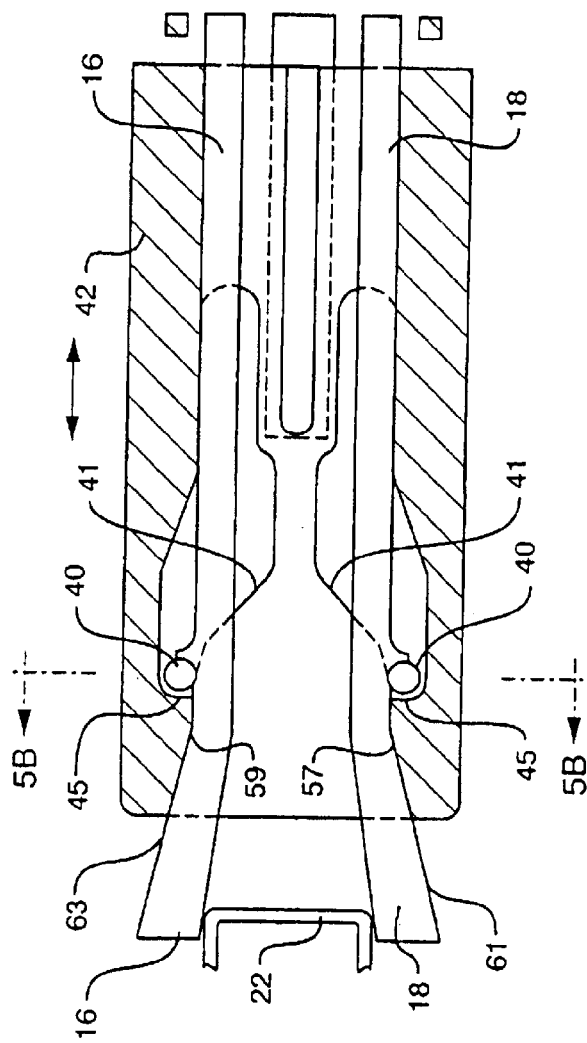
FIG. 5a is a sectional view taken along the lines 5a–5a of FIG. 3b.
Figure 5B:
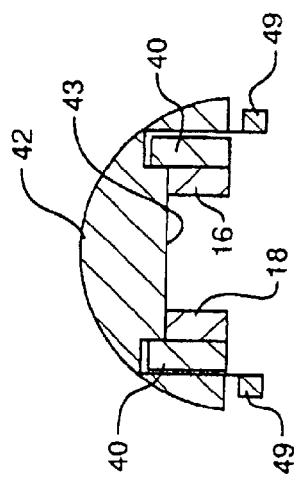
Figure 5C:
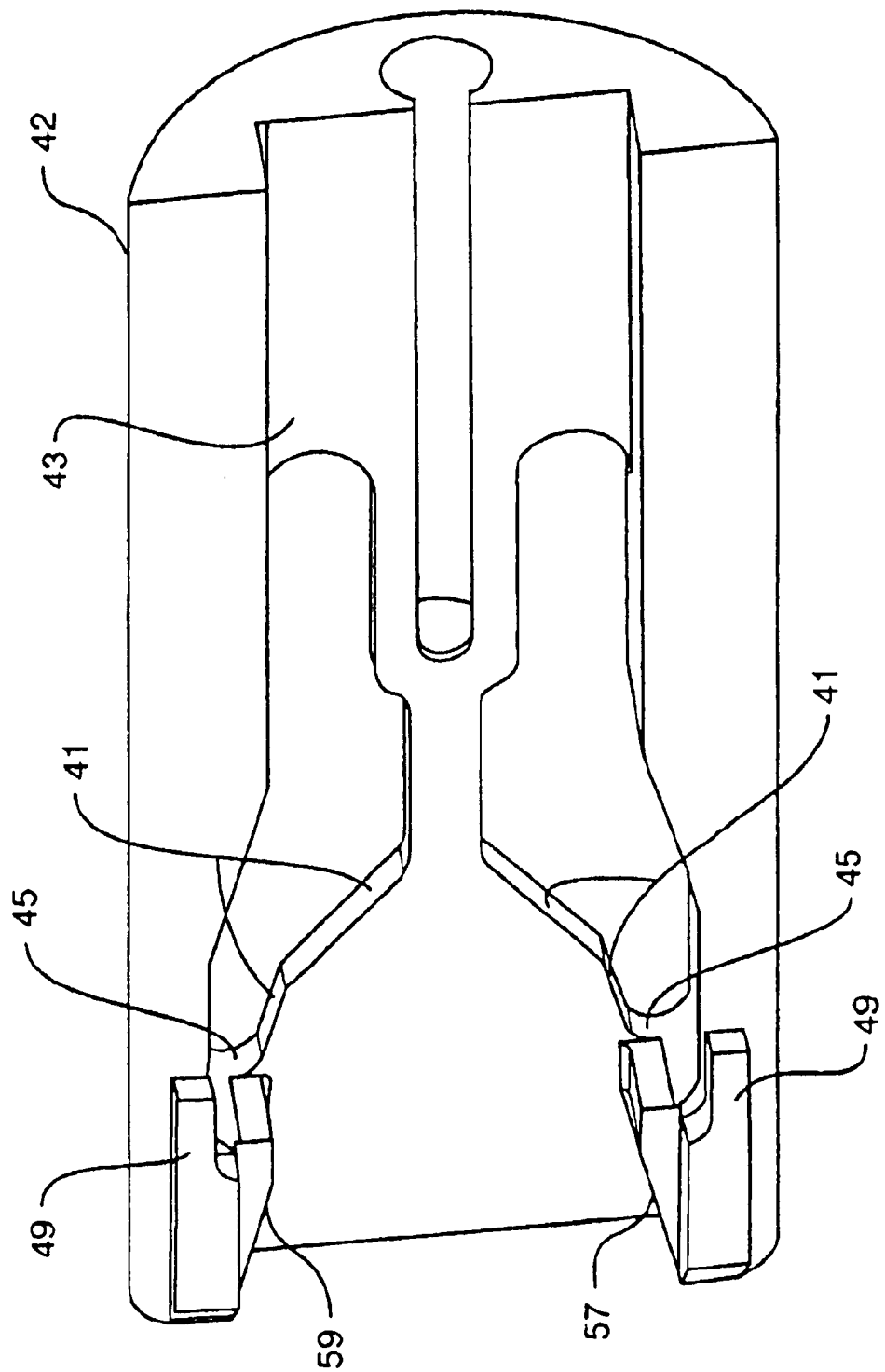
Figure 5D:
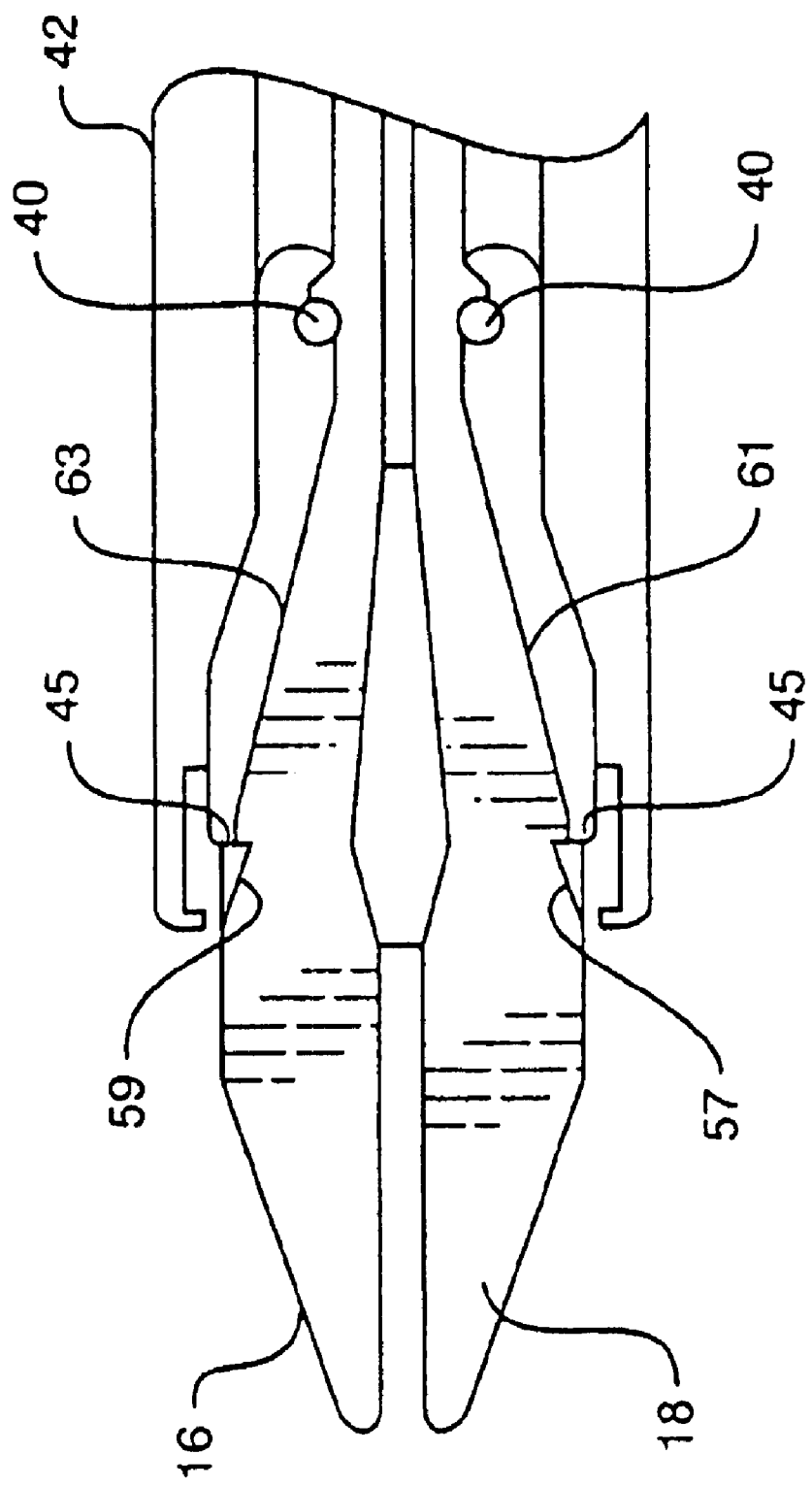
FIG. 5d is a plan view of the cinch and jaws/pins in a jaw closed position.

The jaws 16 and 18 are movably supported between an upper housing half, called a "cinch" 42, and a stationary lower housing half called a "brace" 15. The jaws 16 and 18 each have an upstanding "limiting" pin 40 on each leg thereof, as may be seen in FIGS. 2, 5a, 5b and 5d. Each pin 40 is arranged to slide along a respective cam track 41 disposed on an inner surface wall 43 of the cinch 42. Each pin 40 may reside at least partially in a "pocket" 45 at the distal end of each cam track 41 to limit or prevent inadvertent closure of the jaws 16 and 18 when they are disposed at that point (the cinch 42 fully retracted proximally), with the jaws 16 and 18 fully spread apart. The jaw pins 40, when slid into and mate with the pockets 45 in the distal end of the track 41 in the cinch 42 thus prevent the jaws 16 and 18 from accidentally closing or pinching a clip or staple 22 between those jaws 16 and 18. The pins 40 slide along the track 41 as the cinch 42 is moved proximally and distally. The pins 40 move toward and apart from one another correspondingly, as the jaws 16 and 18 move toward and apart from one another. The cinch 42 has a pair of cam surfaces 57 and 59, which slidingly receive an outer edge 61 and 63, as may be seen in FIGS. 5a and 5d. As the cinch 42 is caused to move distally, the jaws are pinched together by the effect of the cam surfaces 59 and 57 on the cinch 42 acting on the side edges 61 and 63 of the jaws 18 and 16. The relative position of the cinch 42 with the jaws 16 and 18 closed, and its pins 40 in a rearward or proximal position is shown in FIG. 5d. The jaws 16 and 18 being open and the pins 40 in the distal pockets 45, is represented in FIG. 5a. The cinch 42 is always proximally disposed relative to the jaws 16 and 18 before the staples or clips 22 are advanced into the tracks 36 in the jaws 16 and 18. The cinch 42 is shown more clearly in FIG. 5c, with a pair of locking rails 49, as also shown in FIG. 4. The rails 49 each slidably engage a shoulder 51 on the upper side of the brace 51, as shown in FIG. 4. This securement arrangement permits the cinch 42 to be lockably engaged with the brace 15 and secure the jaws 16 and 18, the pusher 20 and like components in a secure manner as the cinch 42 is slid relative to the brace 15 for squeezedly closing and permitting the biased self opening of the jaws 16 and 18. The jaws 16 and 18 are locked into their "open" position when the pins 40 on those jaws 16 and 18 are engaged into the pockets 45 of the tracks 41 of the cinch 42.

The wings 26 on the elongated cross-shaped push member 24 also fit into the same track 36 in the jaws 16 and 18 as do the generally U-shaped clips 22 (the wings 26 entering the track 36 after the staples or clips 22 are pushed therein) do as they are being pushed distally or forwardly and prevent the jaws 16 and 18 from partially closing to undesirably squeeze a staple 22 which might fall into a patient. The jaws 16 and 18 close only after proximal withdrawal of the cross-shaped push member 24 from between the jaws 16 and 18, and distal advance of the cinch 42. This movement or the cinch 42 proximally permits the jaws 16 and 18 to be "un-pinched" and allows their self-opening by the proximally moving cinch 42, so as to allow the jaws 16 and 18 to accept a new, open U-shaped clip member 22, ready for a further clip actuation on a body tissue "T". The wings 26 withdraw from the tracks 36 in the jaws 16 and 18 to allow closure of the jaws 16 and 18 on the clip 22 pushed therebetween.

The jaws 16 and 18 are thus pushed to their "squeezed-closed" position by the distally directed motion of the generally U-shaped cinch 42 on the distal end of a "closing" pushrod 47, as shown in FIGS. 1, 2, 3a, 3b and 5a. The closing pushrod 47 has a proximal end (not shown for clarity) which is connected to the trigger mechanism in the proximal or handle end of the medical clip device 10, which when actuated, effects the proper distal (and subsequent proximal) motion of that pushrod 47.

Figure 6:
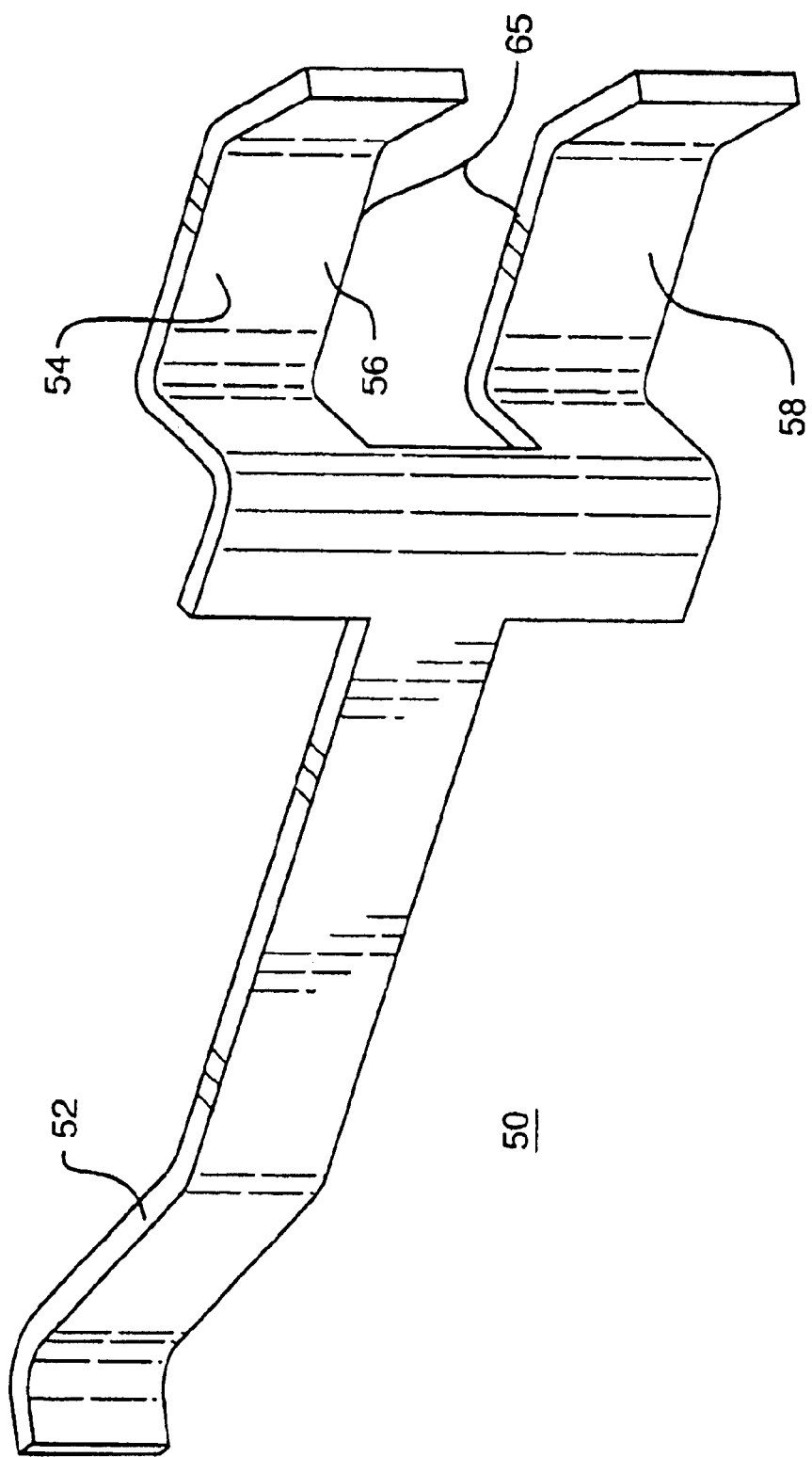
FIG. 6 is a perspective view of a spring bias member of the present invention.
Figure 7:
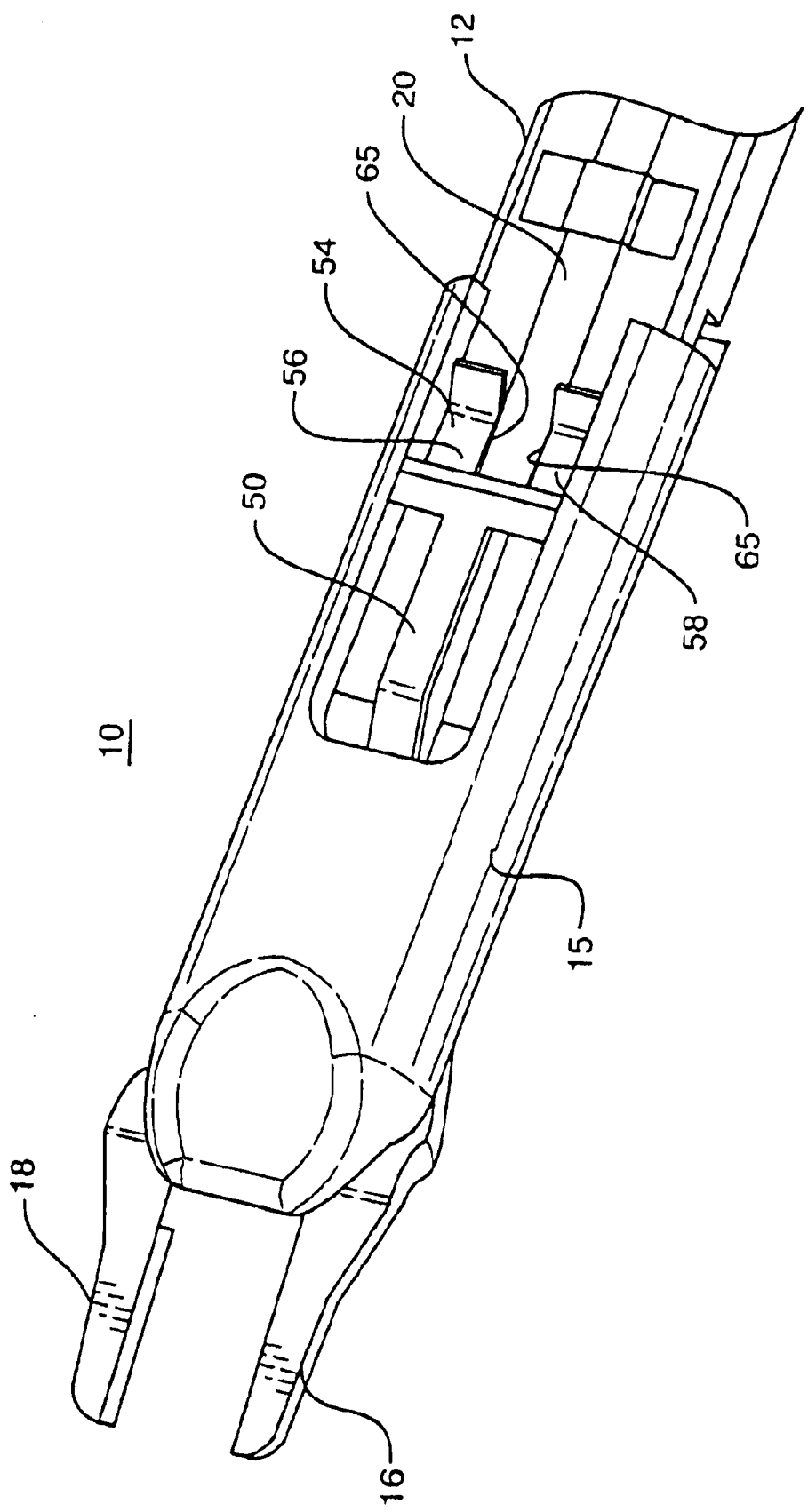
FIG. 7 is a perspective view of the bottom of the clip device shown in FIG. 1.

The lower housing or brace 15 which is disposed in an opposed relationship to the cinch 42, comprises the lower side of the stationary beam 12 or support channel, as may be seen in FIGS. 1, 2, 3b, 3c, 4 and 7. The spring 50, shown in a separate perspective view in FIG. 6, is an elongated member, has a distalmost end 52 which is shaped upwardly, as seen in FIG. 2, to provide a biased finger on the lowermost side of the generally cross-shaped pusher member 24, again as best seen in FIG. 2. The distal end 52 of the spring 50 keeps the pusher 20 right behind the clip 22 and at the proper level therewith, so that the upstanding rails 28 and 30 on the distalmost end of the cross-shaped member 26 does not slip below the bridging portion of the clip 22, which otherwise would lead to possible misfiring or jamming of the clip 22 without binding to tissue "T" and possible loss of the clip 22 in the patient.

The spring 50 has a proximal end 54 which is bifurcated into two parallel legs 56 and 58, which are formed into a generally U-shaped configuration in a longitudinal direction. The legs 56 and 58 each have an inner edge 65 between which the pusher member 20 is slidably guided, as may be seen in FIGS. 2, 3c, 6 and 7. The elongated arm of the clip pusher 20 extends between the bifurcated legs 56 and 58 of the spring 50, as may be best seen however in FIGS. 3c and 7, to center the pusher 20 and keep it in proper alignment.

The distalmost finger 52 of the elongated spring 50 adjacent the brace 15, as may be seen in FIG. 2, is in rubbing, biased engagement with the underside of the generally cross-shaped pusher member 20. The biased spring 50 keeps the elongated cross-shaped pusher member 20 in line with the back or bridging portion of the clip 22. The jaws 16 and 18 are prevented from crossing or misaligning with respect to one another when those jaws 16 and 18 are being squeezed together by the distally directed camming force of the cinch 42 and closing in on a U-shaped clip 22 therebetween. The jaws 16 and 18 are also accurately "opposed" with respect to one another, because of their ultimate relationship with the alignment of the cross-shaped member 24 biased by the spring 50 arranged thereadjacent.

We claim:

1. A medical clip dispenser apparatus for the pinching of a medical clip or staple about a portion of a mammalian body tissue, said apparatus comprising:

an elongated support beam having a distal end with a stationary lower housing thereon;

a distally movable hollow cinch slidably disposed on said lower housing, said cinch having a portion of a pair of openable and closable jaws squeezably arranged therewithin; and an elongated pusher having a generally cross-shaped member on a distal end thereof in slidable engagement with a shoulder track on said jaws, to slide between said jaws as they spread apart from one another and for concurrently pushing a new clip into position between said jaws.

2. The medical clip dispenser as recited in claim 1, wherein each of said jaws has an inner edge with a shoulder track extending therealong, for guided receipt of said clip and for subsequent stabilizing receipt of said cross-shaped member.

3. The medical clip dispenser as recited in claim 2, wherein said cross-shaped member includes a pair of wing members extending therefrom, each of said wing members having an outer edge which mates with said shoulder track to keep prevent premature closing of said jaws after a clip has been fed between said jaws.

4. The medical clip dispenser as recited in claim 3, wherein each of said jaws has an upstanding pin thereon for sliding engagement with a pocket in a cam track in said cinch to prevent accidental closing of said jaws.

5. The medical clip dispenser as recited in claim 4, wherein said cross shaped member has a pair of upstanding rails thereon, each of said rails having a distal edge arranged to push distally a new clip in said shoulder track during distal advancement of said cross-shaped member.

6. The medical clip dispenser as recited in claim 5, wherein each of said rails has a sloped proximal edge to permit said rails to be cammed downwardly and out of the way of a successive clip during proximal movement of said cross-shaped member.

7. The medical clip dispenser as recited in claim 4, wherein said cinch has an inner surface on each of said cam tracks for slidable receipt and release of a pin therefrom to permit said jaws to be temporarily locked in the open position.

8. The medical clip dispenser as recited in claim 3, including an elongated biasing spring secured in said lower housing, said elongated biasing spring having a distal end which is in biased rubbing engagement with a lower side of said cross-shaped member so as to keep said cross-shaped member engaged with said clip during loading thereof between said jaws.

9. The medical clip dispenser as recited in claim 8, wherein said elongated biasing spring has a bifurcated proximal end, said bifurcated proximal end being arranged to straddle said elongated pusher for alignment of said pusher with respect to said biasing spring.

10. The medical clip dispenser as recited in claim 1, wherein said cinch and said lower housing each have interengagable rails to prevent their inadvertent separation from one another.

11. A medical clip dispenser apparatus for the pinching of a medical clip or staple about a portion of a mammalian body tissue, said apparatus comprising:

an elongated support beam having a distal end with a stationary lower housing brace thereon;

a distally movable U-shaped cinch slidably disposed on said lower housing, said cinch having a portion of a pair of closable jaws squeezably arranged therewithin;

an elongated pusher having a generally cross-shaped pusher member on a distal end thereof in slidable engagement with said clip or staple, to push a new clip into position between said jaws; each of said jaws having an inner edge with a shoulder track extending therealong, for guided receipt of said clip and for subsequent receipt of said cross-shaped pusher member; said cross-shaped member including a pair of wing members extending therefrom; said wing members laterally disposed on said cross-shaped member so as to slidably engage said shoulder tracks in said jaws after a clip has been loaded between said jaws; said cross-shaped member comprising a pusher having a pair of upstanding rails thereon, each of said rails having a distal edge arranged to push distally a new clip in a clip track during distal advancement of said cross-shaped member; each of said rails having a sloped proximal edge to permit said rails to be cammed downwardly and out of the way of said clip track during proximal movement of said cross-shaped member; and wherein each of said jaws has an upstanding pin thereon for respective engagement with a pocket in a cam track in said cinch to prevent inadvertent closing of said jaws.

* * * * *